(12) United States Patent
Chang et al.

(10) Patent No.: US 6,602,710 B1
(45) Date of Patent: Aug. 5, 2003

(54) SCREENING METHOD FOR SREBP PATHWAY-SPECIFIC INHIBITORS

(75) Inventors: Ta-Yuan Chang, Etna, NH (US); Tatsuhiko Kodama, Tokyo (JP); Takao Hamakubo, Tokyo (JP); Yoshiki Kawabe, Shizuoka-ken (JP)

(73) Assignees: Chugai Seiyaku Kabushiki Kaisha, Tokyo (JP); Trustees of Dartmouth College, Hanover, NH (US)

( * ) Notice: Subject to any disclaimer, the term of this patent is extended or adjusted under 35 U.S.C. 154(b) by 0 days.

(21) Appl. No.: 09/141,371

(22) Filed: Aug. 27, 1998

(51) Int. Cl.$^7$ .......................... C12Q 1/00; C12P 21/00; C12N 15/09; C12N 15/63
(52) U.S. Cl. .................. 435/375; 435/29.1; 435/7.1; 435/11; 435/70.1; 435/325; 435/69.1; 435/4; 435/320.1; 530/300; 530/350; 536/23.1
(58) Field of Search ............................... 435/29, 7.1, 11, 435/70.1, 325, 375, 69.1, 4, 320.1; 530/350, 300; 536/23.1

(56) References Cited

FOREIGN PATENT DOCUMENTS

| WO | WO94/26922 | * 11/1994 |
|---|---|---|

OTHER PUBLICATIONS

Horton et al., Transgenic Mice Expressing Truncated SREBP–2, vol. 101, No. 11, pp. 2331–2339, (Jun. 1998).
Duncan et al., The Journal of Biological Chemistry, vol. 273., No. 28, pp. 17801–17809, (Jul. 10, 1998).
Sakai et al., The Journal of Biological Chemistry, vol. 273, No. 10, pp. 5785–5793, (Mar. 6, 1998).
B. M. Forman et al., *Cell*, vol. 81, pp. 687–693 (1995).
B. A. Janowski et al., *Nature*, vol. 383, pp. 728–731 (1996).
D. S. Lala et al., *Proc. Natl. Acad. Sci. USA*, vol. 94, pp. 4895–4900 (1997).
J. B. Kim et al., *Proc. Natl. Acad. Sci. USA*, vol. 95, pp. 4333–4337 (1998).
M. T. Hasan et al., *Somat. Cell Mol. Genet.*, vol. 20, No. 6, pp. 481–491 (1994).
Scandinavian Simvastatin Survival Study Group, *The Lancet*, vol. 344, pp. 1383–1389 (1994).
A. M. Gotto, *Am. J. Med.*, vol. 104(2A), pp. 6S–8S (1998).
M. S. Brown et al., *Cell*, vol. 89, pp. 331–340 (1997).
M. T. Hasan et al., *Somat. Cell Mol. Genet.*, vol. 20, No. 3, pp. 183–194 (1994).
J. Sakai et al., *Cell*, vol. 85, pp. 1037–1046 (1996).
R. B. Rawson et al., *Mol. Cell*, (1997) vol. 1, pp. 47–57 (1997).
T. Y. Chang et al., *J. Biol. Chem.*, vol. 255, No. 16, pp. 7787–7795 (1980).
D. R. Illingworth, *Am. J. Cardiol.*, (1993) vol. 72, pp. 54D–58D (1993).

* cited by examiner

*Primary Examiner*—Yvonne Eyler
*Assistant Examiner*—Nirmal S. Basi
(74) *Attorney, Agent, or Firm*—Birch, Stewart, Kolasch & Birch, LLP (57) ABSTRACT

This invention provides a screening method for sterol regulatory element binding protein (SREBP) pathway-specific inhibitors using a mutant cultured cell, as well as therapeutic agents for hyperlipemia, arterial sclerosis, obesity or cancer containing an SREBP pathway-specific inhibitor selected by said screening method.

7 Claims, 5 Drawing Sheets

SCREENING METHOD FOR SREBP PATHWAY-SPECIFIC INHIBITORS

BACKGROUND OF THE INVENTION

The present invention relates to a screening method for SREBP (sterol regulatory element binding protein) pathway-specific inhibitors. The present invention also relates to therapeutic agents for hyperlipemia, arterial sclerosis, obesity or cancer containing an SREBP pathway-specific inhibitor selected by said screening method.

Cholesterol is an essential substance for living bodies as a component of cell membranes or a precursor for syntheses of steroid hormones or bile acids. However, excessive accumulation thereof is fatal for cells, and therefore, homeostatic maintenance of cellular cholesterol level is a very important physiological mechanism. At the level of living bodies, excessive accumulation of cholesterol is also known to cause various diseases such as hyperlipemia or atherosclerosis. The results of a recent large-scale clinical test on cholesterol-lowering drugs showed that the mortality of patients of cardiac diseases is improved by lowering serum cholesterol level, revealing the importance of the maintenance of a proper cholesterol level in living bodies (Scandinavian Simvastatin Survival Study Group, Lancet (1994) 344:1383–1389; Gotto, A. M., Am. J. Med. (1998) 104:6S–8S).

Homeostatic maintenance of cellular cholesterol level is known to occur at various stages such as the level of transcription, translation, enzyme, or the like. Recent discovery of factors involved in transcriptional control of a group of cholesterol synthases or low-density lipoprotein (LDL) receptors dramatically accelerated an understanding of the mechanism of homeostatic regulation of cholesterol at transcriptional level.

LDL receptors or cholesterol synthases such as HMG-CoA reductase are directly responsible for the maintenance of cholesterol level as a gate for cholesterol uptake into cells or a source of newly synthesized cholesterol. It is well known that expression of these factors is feedback-regulated depending on the cholesterol level. Recently, sterol regulatory element binding proteins (SREBPs) that are transcriptional activation factors binding to a sterol regulatory element (SRE) in the promoter domain of these genes was shown to be involved in said regulation (Brown, M. S. and Goldstein, J. L. Cell (1997) 89:331–340).

Figure 1:
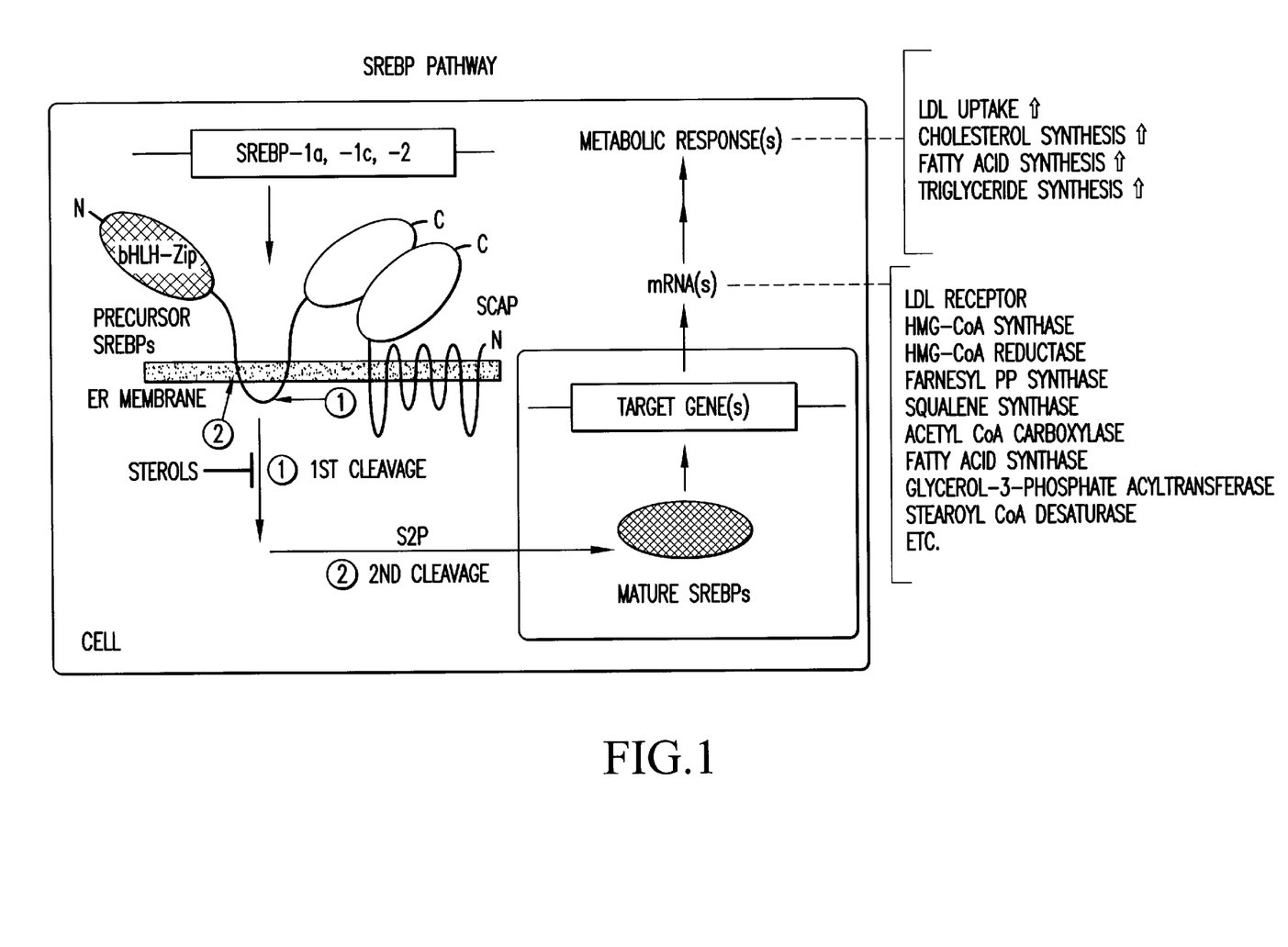
FIG. 1. Schematic representation of the sterol regulatory element binding protein (SREBP) pathway.

SREBP has two isoforms of closely related structures expressed from different genes, SREBP-1 and SREBP-2. Both are expressed as membrane proteins spanning the membrane twice with both ends oriented to the cytosol in the endoplasmic reticulum membrane or nuclear membrane. Upon decrease of cellular cholesterol level, the envelope protein SREBP is thought to be cleaved with proteases in two steps to release the activated N-terminal DNA-binding domain from the membrane, which migrate into the nucleus to activate transcription of target genes (FIG. 1). The protease-catalyzed two-step cleavage mechanism has been mostly unknown. It has been shown that the first step of cleavage is sensitive to cholesterol while the second step (site 2) of cleavage automatically occurs as a result of the first step (site 1) of cleavage.

In M19, which is a mutant cell line of Chinese hamster ovary (CHO)-K1 cells (ATCC: CRL-9618) with lowered cholesterol synthesis and LDL receptor activities (Hasan, M. T. et al., Somat. Cell Mol. Genet. (1994) 20:183–194), a study has shown that no cleavage occurs at site 2 of SREBP (Sakai, J. et al. Cell (1996) 85:1037–1046), and a gene for a protease responsible for cleavage at site 2, S2P has been cloned by complementation using said cell line (Rawson et al., Mol. Cell (1997) 1:47–57). The SREBP sequence cleaved with S2P has not been determined but it is known to lie near the N-terminal first membrane-spanning domain.

On the other hand, the cleavage at site 1 is known to occur between Leu and Ser, but the enzyme per se has not been known. Another mutant cell line of CHO-K1 cells, 25RA (Chang, T. Y. and Limanek, J. S., J. B. C. (1980) 255:7787–7795) is resistant to 25-hydroxycholesterol and does not lead to cell death by cholesterol overload, differing from CHO-K1 cells. On the basis of dominant sterol resistancy of 25RA cells, an SREBP cleavage-activating protein (SCAP) was cloned by using an expression library prepared with 25RA cells. An analysis of the SCAP gene of 25RA cells and CHO-K1 cells revealed that one of two point mutations on the SCAP gene of 25RA cells involved a change from aspartic acid to asparagine at position 443 to enhance SREBP cleavage activity at site 1 without being regulated by sterols. The other mutation was a silent mutation. In other words, cholesterol synthesis or LDL receptor activity is not lowered by sterols in 25RA cells carrying mutations on SCAP because SREBP is cleaved at site 1 even in the presence of excessive sterols, revealing that SCAP has an important function in the SREBP cleavage regulation by cholesterol.

In this way, establishment of mutant cells derived from CHO-K1 promoted an understanding of the mechanism of transcriptional control of cholesterol metabolism. This mechanism is thought to be common to mammalian cells such as human or murine cells.

Target genes for SREBPs as reported include enzymes for the cholesterol synthesis system such as HMG-CoA synthase, HMG-CoA reductase, farnesyl diphosphate synthase, squalene synthase, as well as enzymes for the fatty acid synthesis system such as acetyl CoA carboxylase or fatty acid synthase, enzymes for the triglyceride synthesis system such as glycerol-3-phosphate acyltransferase, and the SREBP-2 gene itself (FIG. 1). This suggests that inhibition of the SREBP pathway may result in inhibition of synthesis of lipids such as cholesterol. This possibility was experimentally verified using sterols such as 25-hydroxycholesterol in cultured cells. However, direct demonstration on individual level has not been made. Moreover, recent reports have shown diversity of target genes for SREBPs, suggesting that the SREBP pathway may be involved in various physiological phenomena, as will be described later.

Despite attempts to develop various cholesterol synthesis inhibitors, many of them have not been successful because of toxicity or other reasons. HMG-CoA reductase inhibitors are among rare cases of success, but their effect to lower serum cholesterol was not evaluated as sufficient (Illingworth, D. R., Am. J. Cardiol. (1993) 72:54D–58D). At present, HMG-CoA reductase inhibitors and bile acid reabsorption inhibitors are mainly used for therapy of hyperlipemia. Both drugs decrease serum cholesterol by lowering cholesterol in the liver and activating low-density lipoprotein (LDL) receptors. However, the effect is attenuated by cholesterol uptake into the liver following activation of LDL receptors and no potent cholesterol-lowering effect can be obtained in any case, because these drugs rely on an indirect mechanism of lowering cholesterol in the liver to activate LDL receptors. On the other hand, the results of a large-scale clinic test on serum cholesterol-lowering drugs based on said inhibitors indicated benefits of lowering serum cholesterol in patients with cardiac diseases and raised expectations for more potent cholesterol-lowering drugs.

From this background, we assumed that lipid-lowering agents inhibiting lipid synthesis such as cholesterol synthesis by inhibiting the SREBP pathway may be very useful therapeutic agents for hyperlipemia and also useful for therapy of arterial sclerosis. In view of the fact that intermediate products or metabolic products of the cholesterol synthesis system expressed at a level controlled by SREBPs have been reported to be ligands for PPARs (peroxisome proliferator activated receptors), orphan receptors (Forman, B. M. et al., Cell (1995) 81:687–693; Janowski, B. A. et al., Nature (1996) 383:728–731; Lala, D. S. et al., Proc. Natl. Acad. Sci. U.S.A. (1997) 94:4895–4900), it is useful to use said mechanism for therapy of diseases caused by a decrease in these molecules. Inhibition of the SREBP pathway also seems to be useful for therapy of obesity, since PPARγ was shown to be an important determinant for differentiation to adipocytes and activation of PPAR (Peroxisome Proliferator Activated Receptor) potentially induced by activation of SREBP was also reported (Kim, J. B. et al., Proc. Natl. Acad. Sci. U.S.A. (1998) 95:4333–4337). Inhibition of the SREBP pathway also seem to be applicable as anticancer agents since some intermediate products of the cholesterol synthesis system are used to modify Ras or other genes playing an important role in cell growth. Thus, inhibition of the SREBP pathway may be promising for therapy of various diseases.

However, any convenient screening method for inhibitors of this pathway has not been known up to the present. Noting the above-mentioned 25RA and M19 cells as well as DM7 cells carrying mutations of said two cell lines (Hasan, M. T. et al., Somat. Cell Mol. Genet. (1994) 20:481–491), we examined the potential of a screening system for SREBP pathway-specific cholesterol synthesis inhibitors using these cells having mutations in the SREBP pathway and designed a convenient screening system.

SUMMARY OF THE INVENTION

The present invention provides a screening method for SREBP pathway-specific inhibitors using a mutant cultured cell.

A preferred first embodiment of the screening method of the present invention is a screening method for SREBP pathway-specific inhibitors, comprising assaying both cholesterol synthesis and LDL receptor activities using a cell in which SREBP cleavage activating protein (SCAP) has lost response to sterols.

A preferred second embodiment of the screening method of the present invention is a screening method for sterol-like SREBP pathway-specific inhibitors using a combination of a cell in which SCAP has lost response to sterols and a cell in which SCAP has not lost response to sterols.

A preferred third embodiment of the screening method of the present invention is a screening method for SREBP pathway-specific inhibitors using a combination of a cell lacking SREBP Site 2 protease (S2P) and a S2P-carrying cell.

A preferred fourth embodiment of the screening method of the present invention is a screening method for SREBP pathway-specific inhibitors using a cell in which a chimeric gene of a reporter gene and the gene encoding the C-terminus of SREBP has been expressed.

A preferred fifth embodiment of the screening method of the present invention is a screening method for sterol-like SREBP pathway-specific inhibitors, comprising screening for SREBP pathway-specific inhibitors using a cell in which a chimeric gene of a reporter gene and the gene encoding the C-terminus of SREBP has been expressed, and then screening for sterol-like SREBP pathway-specific inhibitors using a cell in which SCAP has lost response to sterols and the same chimeric gene has been expressed.

A preferred sixth embodiment of the screening method of the present invention is a screening method for S2P-specific inhibitors using a cell in which a chimeric gene of a reporter gene and the gene encoding the stretch from the first transmembrane domain of SREBP to the cleavage site with SREBP Site 1 protease (S1P) has been expressed.

The present invention also provides a vector obtained by inserting a chimeric gene of a reporter gene and the gene encoding the C-terminus of SREBP into a reporter gene expression vector.

The present invention also provides a vector obtained by inserting a chimeric gene of a reporter gene and the gene encoding the stretch from the first transmembrane domain of SREBP to the cleavage site with SREBP Site 1 protease (S1P) into a reporter gene expression vector.

The present invention also provides SREBP pathway-specific inhibitors obtained by the screening method of the present invention.

The present invention also provides therapeutic agents for hyperlipemia containing thus obtained SREBP pathway-specific inhibitors.

The present invention also provides therapeutic agents for arterial sclerosis containing thus obtained SREBP pathway-specific inhibitors.

The present invention also provides therapeutic agents for obesity containing thus obtained SREBP pathway-specific inhibitors.

The present invention also provides therapeutic agents for cancer containing thus obtained SREBP pathway-specific inhibitors.

DETAILED DESCRIPTION OF THE INVENTION

Suitable cells for the screening method of the present invention are first described. Cells used in the screening method of the present invention are, for example, the above-mentioned Chinese hamster ovary (CHO)-K1 cells (ATCC: CRL-9618) and mutant cultured cells thereof.

However, the SREBP pathway is considered as a common mechanism to mammals as described above, and therefore, the invention is not limited to these cells derived from CHO-K1.

Suitable cells in which SCAP has lost response to sterols include but are not limited to, for example, the above-mentioned 25RA that is a mutant cell line of CHO-K1 cells. 25RA cells carrying mutated SCAP always keep SREBP in activated state so that they are not regulated in response to sterols. That is, SREBP is not inactivated in such cells even when cholesterol is excessive.

Suitable cells lacking SREBP Site 2 protease (S2P) include but are not limited to, for example, the above-mentioned M19 that is a mutant cell line of CHO-K1 cells. In M19 cells lacking S2P, SREBP is not activated and no response to sterols occurs. That is, SREBP is not activated even when cholesterol is lacked. Suitable cells having similar properties include SRD6 (Evans, M. J. and Metherall, J. E., Mol. Cell Biol. (1993) 13:5175–5185).

Suitable cells having both of these mutations include but are not limited to, for example, the above-mentioned DM7 derived from CHO-K1 cells. That is, DM7 is a cell line in which SCAP has lost response to sterols and S2P is lacked.

Properties of typical cultured cells used in the present invention are collated in the following Table 1, wherein + represents the presence of mutation and − represents the absence of mutation.

TABLE 1

| Cell line | Lack of S2P | Enhanced SCAP (non-responsive to sterols) |
|---|---|---|
| CHO-K1 | − | − |
| M19 | + | − |
| 25RA | − | + |
| DM7 | + | + |

In the screening method of the present invention, these mutant cell lines and CHO-K1 cells with no mutation (ATCC: CRL-9618) can be appropriately used alone or in combination. For example, the above-mentioned second embodiment of screening can be accomplished by a combination of 25RA cells and CHO-K1 cells, and the third embodiment can be accomplished by a combination of M19 cells and CHO-K1 cells or a combination of DM7 cells and 25RA cells.

25RA cells, M19 cells and DM7 cells have been deposited with the National Institute of Bioscience and Human-Technology of the Agency of Industrial Science and Technology residing at 1–3, Higashi 1-Chome, Tsukuba-city, Ibaraki-prefecture, 305-8566, Japan) on May 19, 1998 under accession numbers FERM BP-6361, FERM BP-6362 and FERM BP-6363, respectively.

(1) Screening According to the First Embodiment

The first embodiment of the present invention comprises screening for SREBP pathway inhibitors by assaying both cholesterol synthesis and LDL receptor activities using a cell in which SCAP has lost response to sterols.

The screening method for SREBP pathway-specific inhibitors according to this embodiment comprises the steps of:

(a) culturing a cell in which SCAP has lost response to sterols in the presence and absence of a test drug for SREBP pathway inhibitor, and (b) measuring both cholesterol synthesis activity and LDL receptor activity of said cell.

Any compound that inhibits both cholesterol synthesis activity and LDL receptor activity in cells in which SCAP has lost response to sterols is highly likely to be an SREBP pathway inhibitor.

Suitable cells in which SCAP has lost response to sterols may include 25RA cells, for example. In SP2-deficient M19 cells in which both cholesterol synthesis activity and LDL receptor activity are extremely lowered, both activities also seem to be lowered by SREBP pathway inhibitors. Although both activities can also be assayed in ordinary cultured cells, it is difficult to remove false-positive samples that indirectly inhibit the SREBP pathway because the activity of the SREBP pathway varies with intracellular cholesterol level in these cells. For example, acyl-CoA: cholesterol acyl transferase (ACAT) inhibitors lower both activities by increasing cellular free cholesterol. However, such false positive samples are less likely to occur in cells in which SCAP has lost response to sterols, such as 25RA cells, which are therefore suitable for screening according to this embodiment.

(2) Screening According to the Second Embodiment

The second embodiment of the present invention comprises screening for sterol-like SREBP pathway inhibitors using a combination of a cell in which SCAP has lost response to sterols and a cell in which SCAP has not lost response to sterols.

The screening method for SREBP pathway-specific inhibitors according to this embodiment comprises the steps of:

(a) culturing a cell in which SCAP has lost response to sterols and a cell in which SCAP has not lost response to sterols cell in the presence of a test drug for sterol-like SREBP pathway inhibitor, and (b) measuring the cholesterol synthesis activity or LDL receptor activity of said both cells.

For example, suitable cells in which SCAP has lost response to sterols include 25RA cells and suitable cells in which SCAP has not lost response to sterols include CHO-K1 cells.

In ordinary cells that are responsive to sterols, cholesterol synthesis or LDL receptor activity is lowered by sterol-like SCAP inactivation effect. In cells that have lost response to sterols, however, cholesterol synthesis or LDL receptor activities is not lowered even under sterol-like SCAP inactivation effect because SCAP is not inactivated. Properties of such cells can be used to screen for test drugs inhibiting the SREBP pathway like sterols by measuring the cholesterol synthesis activity or LDL receptor activity of a cell in which SCAP has lost response to sterols and a cell in which SCAP has not lost response to sterols. According to this method, cholesterol synthase inhibitors that are positive in ordinary cells also inhibit cholesterol synthesis in cells that are not responsive to sterols so that they can be readily discriminated from each other.

(3) Screening According to the Third Embodiment

The third embodiment of the present invention comprises screening for SREBP pathway inhibitors using a combination of an S2P-deficient cell and a S2P-carrying cell.

The screening method for SREBP pathway-specific inhibitors according to this embodiment comprises the steps of:

(a) culturing an S2P-deficient cell and a S2P-carrying cell in the presence of a test drug for SREBP pathway inhibitor, and (b) measuring the cholesterol synthesis activity or LDL receptor activity of said both cells.

Suitable combinations of an S2P-deficient cell and a S2P-carrying cell include, for example, a combination of M19 cells and CHO-K1 cells or a combination of DM7 cells and 25RA cells.

In ordinary cells carrying S2P, cholesterol synthesis or LDL receptor activity is lowered by S2P inhibitors. In S2P-deficient cells, however, cholesterol synthesis or LDL receptor activity is no more lowered even by inhibition of the SREBP pathway because S2P has already been inactivated. Properties of such cells can be used to screen for test drugs inhibiting S2P by measuring the cholesterol synthesis activity or LDL receptor activity of ordinary cells and S2P-deficient cells. According to this method, cholesterol synthase inhibitors that are positive in ordinary cells also inhibit cholesterol synthesis in S2P-deficient cells so that they can be readily discriminated from each other.

(4) Screening According to the Fourth Embodiment

Although screening methods according to the first to third embodiments as described above can be used to conveniently screen for SREBP pathway inhibitors, the SREBP pathway has been explained only recently and still unknown in many aspects. Therefore, it is more useful to use SREBP itself for screening for inhibitors specific to the SREBP activation mechanism. In this respect, the reporter gene assay using SRE is effective, but SREBP alone weakly binds to SRE and should act synergistically with co-activators such as transcriptional activator SP1 (specific protein 1) or transcriptional activator NF-Y (nuclear factor Y) for stronger binding, which causes false positive reactions.

If the N-terminal DNA-binding domain (DBD) that is unnecessary for cleavage of SREBP with S1P and S2P is replaced by another reporter to detect release of SREBP from the membrane, SREBP activation can be detected more specifically and more sensitively.

Accordingly, the fourth embodiment of the present invention comprises screening for SREBP pathway-specific inhibitors using a cell in which a chimeric gene of a reporter gene and the gene encoding the C-terminus of SREBP has been expressed.

The screening method for SREBP pathway-specific inhibitors according to this embodiment comprises the steps of:
  (a) introducing a chimeric gene of a reporter gene and the gene encoding the C-terminus of SREBP into a cell in which SCAP has not lost response to sterols,
  (b) culturing said cell in the presence of a test drug for SREBP pathway inhibitor to allow the cell to express said chimeric gene, and
  (c) measuring any signal generated by said reporter gene.

Suitable reporter genes include, for example, green fluorescence protein gene carrying a nucleus localization signal (NLS) sequence or GAL4/VP16 fusion gene. Suitable cells into which the chimeric gene of a reporter gene and the gene encoding the C-terminus of SREBP is expressed include, for example, cells in which SCAP has not lost response to sterols, such as CHO-K1 cells or M19 cells.

Human SREBP-2 has been shown to undergo sterol-regulated cleavage even if the amino acids up to position 472 are replaced by Ras (Sakai et al., Cell (1996) 85 1037–1046). It has also been shown that 8 amino acids in the region 455–483 and the region 402–477 in SREBP-1a and SREBP-2, respectively, are unnecessary for sterol-regulated cleavage (Hua et al., J. Biol. Chem. (1996) 271 10379–10384). This indicates that any protein fused to the C-terminal region from position 484 in human SREBP-1 or position 478 in human SREBP-2 may be cleaved with S1P and S2P. One of such reporters is a protein fused to a fluorescence protein, green fluorescence protein (GFP) (Hamakubo et al., Atherosclerosis (1997) 134:350). However, this fusion protein is not suitable for quantitative assay of cleavage activity, because it is released from the endoplasmic reticulum membrane and diffused into the cytoplasm after cleavage. Thus, we designed a more sensitive fusion protein by introducing a nucleus localization signal (NLS) sequence into GFP so that released GFP migrates to the nucleus, which in turn generates fluorescence.

Namely, a gene in which DBD of SREBP is replaced by NLS-containing GFP is inserted into an appropriate expression vector and the vector is transferred into a cell by a known method to allow it to express said gene. When SREBP is cleaved with S2P, fluorescence migrates to the nucleus. Thus, screening can be accomplished by measuring change of fluorescence amount in the nucleus of a cell treated with a test drug.

If DBD of SREBP is replaced by a factor having a stronger transcriptional activity alone, a reporter gene corresponding to this transcription factor can be introduced to measure the activity of the SREBP pathway as reporter activity. For example, a fusion protein of DBD of GAL4 and the activation domain (AD) of VP16 is known to strongly activate genes downstream of a yeast-specific GAL4-specific sequence (UAS$_G$) (Sadowski et al., Gene (1992) 118:137–141), and suitable for this purpose. That is, a gene in which DBD of SREBP is replaced by said protein is introduced with a reporter gene such as UAS$_G$-luciferase and expressed in cells, so that luciferase activity increases when SREBP is cleaved with S2P. Thus, screening can be accomplished by measuring change of luciferase activity after treatment with a test drug.

Figure 2:
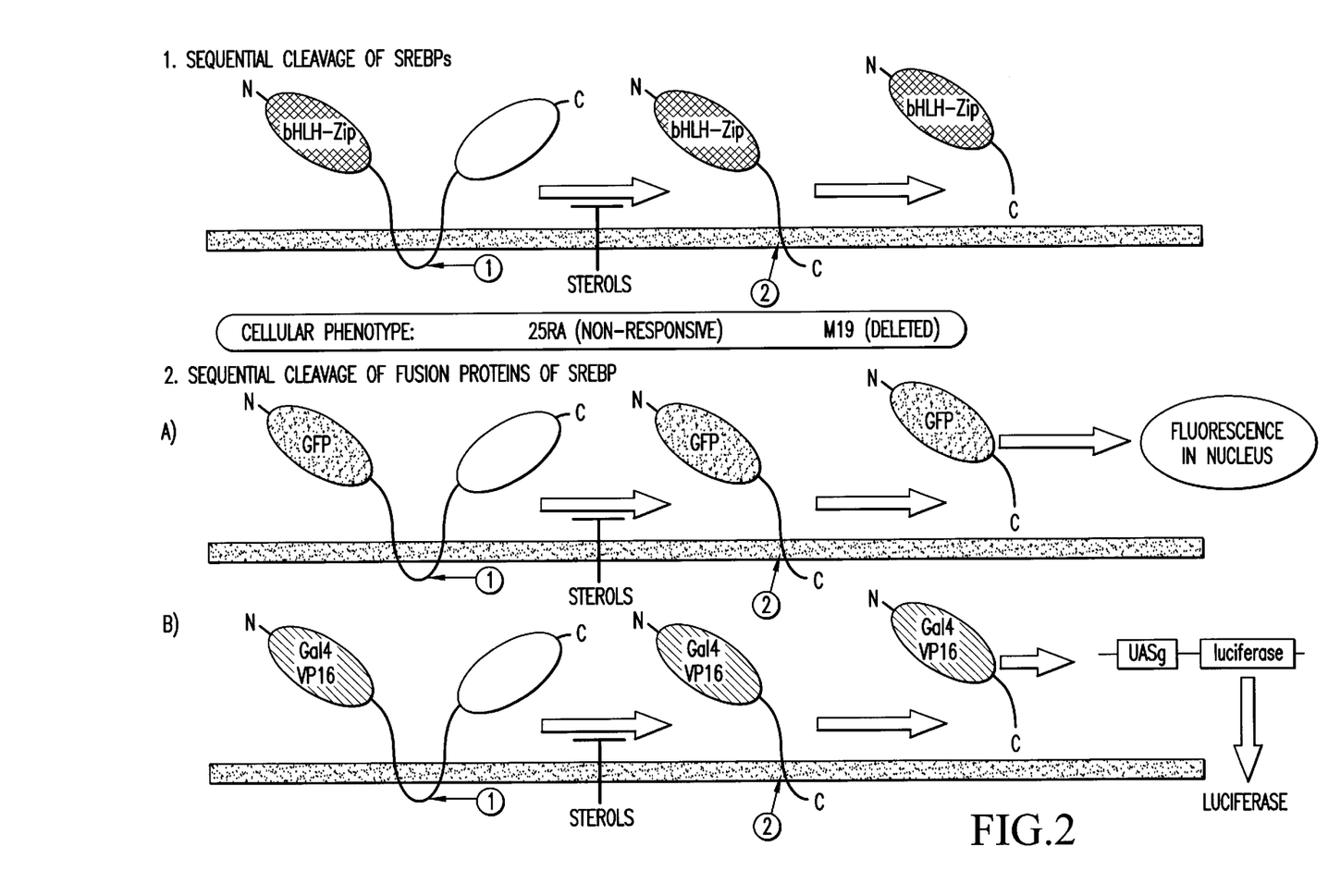
FIG. 2. Sequential cleavage schemes of SREBPs with S1P and S2P as well as sequential cleavage schemes of SREBPs with a fusion protein produced by introducing and expressing a chimeric gene according to an embodiment of the present invention.

FIG. 2 show sequential cleavage schemes of SREBPs by S1P and S2P as well as a sequential cleavage schemes of SREBPs by a fusion protein produced by introducing and expressing a chimeric gene according to the present embodiment.

(5) Screening According to the Fifth Embodiment

Although the SREBP chimeric gene used in the above fourth embodiment may be usefully introduced and expressed in ordinary cells in terms of response to sterols, i.e. a cell in which SCAP has not lost response to sterols, it is more preferable to express said chimeric gene into a cell in which SCAP has lost response to sterols, such as 25RA cells, because the SREBP activation mechanism of ordinary cells is influenced by cholesterol as described above.

Accordingly, the fifth embodiment of the present invention allows more reliable screening for sterol-like SREBP pathway-specific inhibitors, by performing screening according to the fourth embodiment, then expressing the same chimeric gene in a cell in which SCAP has lost response to sterols to perform screening according to the fourth embodiment, and comparing the two screenings. That is, any test drug that was positive in ordinary cells but negative in cells non-responsive to sterols seems to have a sterol-like SREBP pathway-specific inhibitory effect.

The screening method for SREBP pathway-specific inhibitors according to this embodiment comprises the steps of:
  (a) introducing a chimeric gene of a reporter gene and the gene encoding the C-terminus of SREBP into a cell in which SCAP has not lost response to sterols,
  (b) culturing the cell of step (a) in the presence of a test drug for sterol-like SREBP pathway inhibitor to allow the cell to express said chimeric gene,
  (c) measuring any signal generated by said reporter gene,
  (d) introducing the same chimeric gene as used in step (a) into a cell in which SCAP has lost response to sterols, (e) culturing the cell of step (d) in the presence of a test drug for sterol-like SREBP pathway inhibitor to allow the cell to express said chimeric gene, (f) measuring any signal generated by said reporter gene, and (g) comparing the signal measured in step (c) and the signal measured in step (f).

(6) Screening According to the Sixth Embodiment

The sixth embodiment of the present invention comprises screening for S2P-specific inhibitors using a cell in which a chimeric gene of a reporter gene and the gene encoding the stretch from the first transmembrane domain of SREBP to the cleavage site with SREBP Site 1 protease (S1P) has been expressed.

As already described, cleavage of SREBP occurs in two steps and the second step of cleavage with S2P is said to essentially involve cleavage with S1P and automatically occur after cleavage with S1P. Thus, screening for S2P-specific inhibitors can be accomplished by expressing a chimeric gene of a reporter gene (such as GFP-NLS, GAL4-VP16) fused to a gene encoding the stretch from the first transmembrane domain of SREBP to the cleavage site with SREBP Site 1 protease (S1P) as described above in a cell to use it in the same manner as described for screening according to the fourth or fifth embodiment.

The screening method for SREBP pathway-specific inhibitors according to this embodiment comprises the steps of:

(a) introducing a chimeric gene of a reporter gene and a gene encoding the stretch from the first transmembrane domain of SREBP to the cleavage site with SREBP Site 1 protease (S1P) into a cell which does not lack S2P, (b) culturing said cell in the presence of a test drug for SREBP pathway inhibitor to allow the cell to express said chimeric gene, and (c) measuring any signal generated by said reporter gene.

Means for Measuring Cholesterol Synthesis Activity

In order to measure cholesterol synthesis activity, the examples of the present invention use:

(1) amophotericin B cytotoxicity assay, or
(2) $^{14}$C-acetate incorporation assay.

The amphotericin B cytotoxicity assay involves measuring cholesterol synthesis activity, based on the property of amphotericin B to bind to cholesterol in cell membranes and cytotoxically act in proportion to cholesterol level in cell membranes whereby cells can survive at low cholesterol synthesis activity but die at high synthesis activity. That is, the lower the cell survival after treatment with amphotericin B, the higher the cholesterol synthesis activity.

On the other hand, the $^{14}$C-acetate incorporation assay involves measuring $^{4}$C-cholesterol level increasing as cells exploit $^{14}$C-acetate added to the culture medium for cholesterol synthesis.

Alternatively, cholesterol content in cells may be directly assayed, and the present invention is not limited to the two assays used herein.

Means for Measuring LDL Receptor Activity

In order to measure LDL receptor activity, the examples of the present invention use the $^{125}$I-LDL binding assay. However, other suitable means may include incorporation of LDL labeled with a fluorescent lipid DiI into cells or ELISA-mediated measurement of the amount of LDL receptors expressed on the surface of cell membranes, and the screening system of the present invention is not specifically limited to those shown herein.

SREBP pathway-specific inhibitors obtained by the screening method of the present invention are useful as therapeutic agents for hyperlipemia, arterial sclerosis, obesity, cancer, etc. The administration route is suitably oral for therapy of hyperlipemia, arterial sclerosis and obesity, or oral or intravenous as anti-cancer agents. The daily dosage may vary from 0.1 mg to 500 mg, preferably 1 mg to 100 mg per adult. However, the dosage and administration route are not specifically limited to those indicated herein, but should be appropriately chosen according to various factors such as the disease to be treated, medical condition of the patient, physical properties of the resulting SREBP pathway-specific inhibitor or the strength of inhibitory action.

The following examples further explain the present invention in detail, but are not construed as limiting the scope thereof. Various modifications or changes are obvious for those skilled in the art on the basis of the disclosure herein and information available in the field of art, and those are also encompassed in the scope of the present invention.

EXAMPLE

Example 1

Screening Method According to the First Embodiment

In order to assess the availability of this method, an inhibitor of a rate-limiting enzyme for cholesterol synthesis system HMG-CoA reductase, simvastatin, was examined as a test drug. In addition to 25RA cells, DM7 cells were also examined as a cell model treated with an SREBP pathway inhibitor.

Influences on cholesterol synthesis activity of 25RA cells in the presence or absence of simvastatin and DM7 cells in the absence of simvastatin were first determined by the amphotericin B cytotoxicity assay.

On day 0, 25RA and DM7 cells were seeded in 96-well plates at a density of $5 \times 10^3$ cells/well, and incubated overnight in F12 containing 10% LPDS (L-F12) for 25RA or Ham's F12 medium containing 10% FBS (F-F12) for DM7. On day 1, the media were replaced by L-F12 containing simvastatin at various concentrations (0–0.3 $\mu$M) and incubation was continued for 24 hours. On day 2, cells were washed with PBS, and then incubated in PBS containing amphotericin B at various concentrations. After incubation for 4 hours, the cells were washed with PBS and protein content in each well was measured by the Lowry method to assay amphotericin B sensitivity. Amphotericin B sensitivity was expressed as a value (%) when the remaining protein content in each well after the same treatment in the absence of amphotericin B was counted as 100%.

Then, influences on LDL receptor activity of 25RA cells in the presence or absence of simvastatin and DM7 cells in the absence of simvastatin were determined by the $^{125}$I-LDL binding assay. $^{125}$I-LDL was prepared as described by Kawabe et al. (Kawabe, Y. et al., Arch. Biochem. Biophys. (1994) 310:489–496). On day 0, cells were seeded on 6-well plates at a density of $3 \times 10^4$ cells/well, and incubated in F-F12. On day 3, the medium was replaced by L-F12 (containing 20 $\mu$M oleic acid) each containing (a) 1 $\mu$g/ml 25-hydroxycholesterol and 10 $\mu$g/ml cholesterol, (b) 0.1% EtOH or (c) 1 $\mu$M simvastatin, and incubation was continued for 24 hours. On day 4, the cells were incubated at 4° C. for 2 hours, and then washed twice with PBS. Then, incubation was continued at 4° C. in L-F12 (containing 10 mM Hepes-NaOH, pH 7.4) containing 10 $\mu$g/ml $^{125}$I-LDL or 10 $\mu$g/ml $^{125}$I-LDL and 400 $\mu$g/ml LDL. After 5 hours, the cells were washed with buffer B (150 mM NaCl, 50 mM Tris-HCl, 2 mg/ml BSA, pH 7.4), then buffer C (150 mM NaCl, 50 mM Tris-HCl, pH 7.4) each three times, and incubated with 1 ml of buffer D (50 mM NaCl, 10 mM Hepes-NaOH, 4 mg/ml dextran sulfate, pH 7.4) at 4° C. After one hour, buffer D was recovered and assayed for its radioactivity. The protein level in cells remaining in wells was measured by the BCA method to calculate $^{125}$I-LDL binding per mg of cells.

Figure 3:
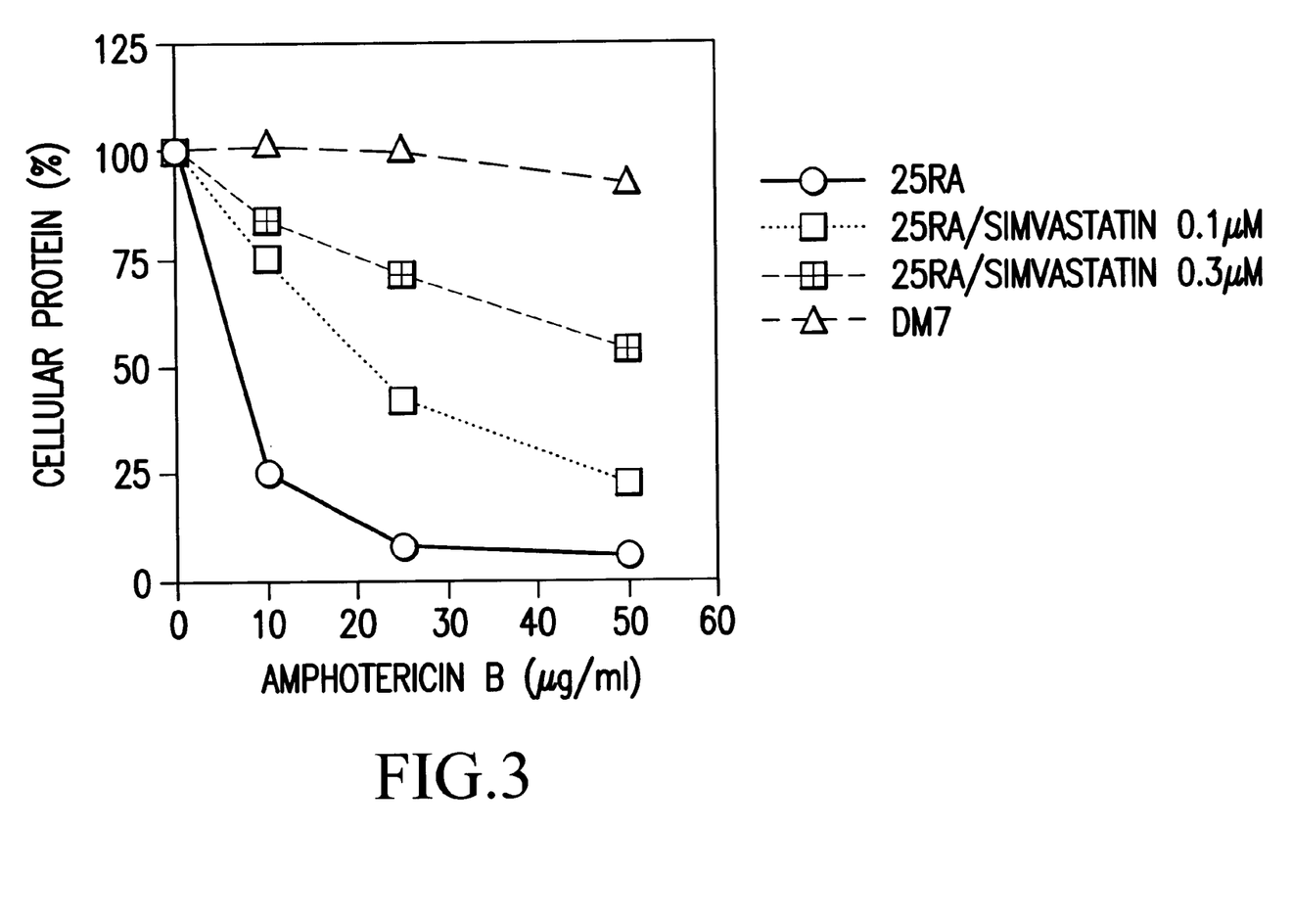
FIG. 3. A graph showing the relation between the concentration of amphotericin B and survival of 25RA cells in the presence or absence of simvastatin and DM7 cells in the absence of simvastatin.

As the results in FIG. 3, survival of 25RA cells decreased depending on the concentration of amphotericin B. However, DM7 showed remarkable resistance to amphotericin B as compared with 25RA. Simvastatin inhibited amphotericin B-induced decrease of survival of 25RA cells concentration-dependently.

As to LDL receptor activity, 25RA showed higher 125I-LDL binding than CHO-K1 in the presence of sterols, as shown in Table 2. $^{125}$I-LDL binding of CHO-K1 was increased by simvastatin treatment, but $^{125}$I-LDL binding of 25RA was unchanged.

TABLE 2

| | Cell surface binding of [$^{125}$I]LDL | | |
|---|---|---|---|
| Sterols | + | − | − |
| Simvastain | − | − | + |
| CHO-KI | 12.5 | 18.1 | 30.1 |
| 25RA | 19.0 | 17.9 | 20.9 | ng/mg protein

As a result, a HMG-CoA reductase inhibitor, simvastatin, had an inhibitory effect against cholesterol synthesis activity but no effect to decrease LDL receptor activity in 25RA. On the other hand, a cell model treated with an SREBP pathway inhibitor, DM7, showed a lower cholesterol synthesis activity than 25RA. As has been already reported, DM7 shows a remarkably low $^{125}$I-LDL binding such as 1/5.5 of 25RA (Hasan, M. T. et al., Somat. Cell Mol. Genet. (1994) 20 481–491). Thus, an experimental system assaying cholesterol synthesis and LDL receptor activities using 25RA cells proved to be a useful system that can specifically detect SREBP pathway inhibitors.

Example 2

Screening Method According to the Second Embodiment

The effects of 25-hydroxycholesterol on cholesterol synthesis activity in CHO-K1 and 25RA were examined. Cells were treated with 0.1 μg/ml of 25-hydroxycholesterol for 24 hours before amphotericin B was added. Cholesterol synthesis activity was measured by the amphotericin B cytotoxicity assay in the same manner as the preceding example.

Figure 4A:
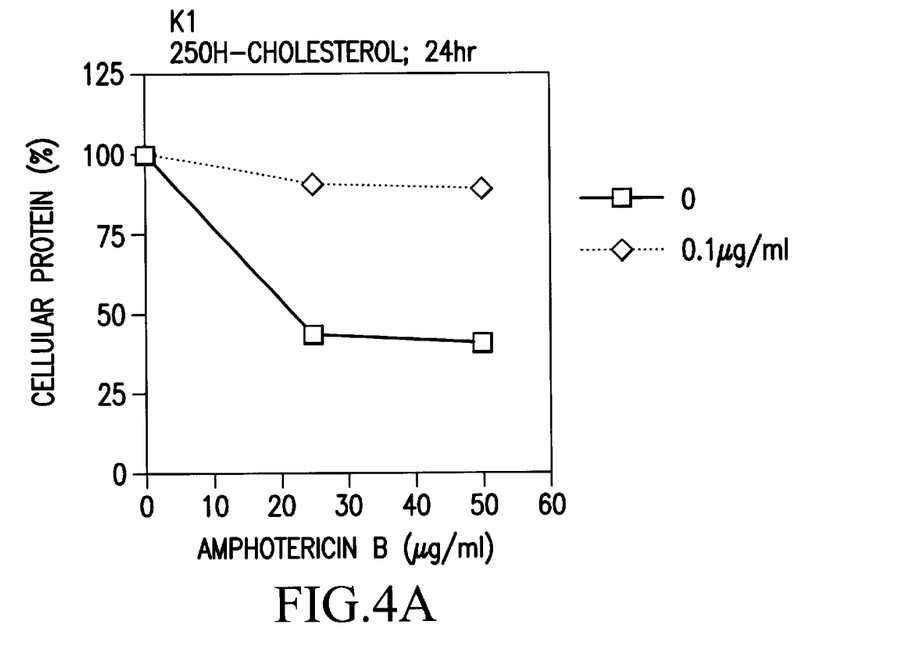
FIGS. 4A–4B. Graphs showing the effects of 25-hydroxycholesterol on cholesterol synthesis activity in CHO-K1 cells and 25RA cells. Cholesterol synthesis activity was measured by the amphotericin B cytotoxicity assay.
Figure 4B:
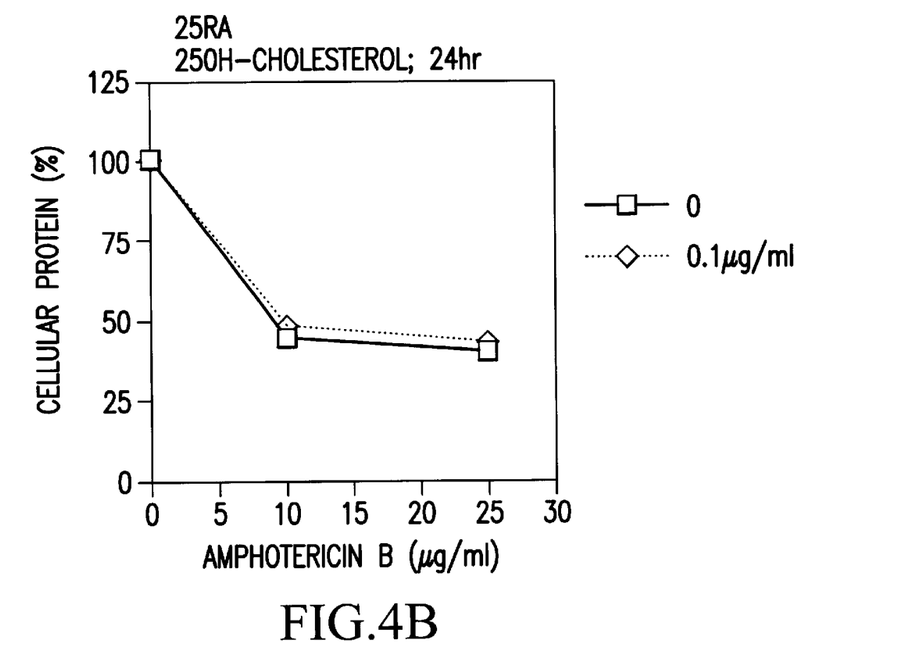

As shown in FIGS. 4A–4B, 25-hydroxycholesterol inhibited cholesterol synthesis activity in CHO-K1 but not in 25RA. This demonstrated that a cholesterol synthesis activity assay using these two cell lines is a useful system that can specifically detect sterol-like SREBP pathway inhibitors.

Example 3

Screening Method According to the Third Embodiment

Cholesterol synthesis activity in CHO-K1 cells and M19 cells was examined using simvastatin as a test drug. The cholesterol synthesis activity was measured by the $^{14}$C-acetate incorporation assay.

On day 0, 5×10$^5$ cells were seeded in 25 cm$^2$ flasks and incubated in F-F12 containing 10% FBS. On day 2, the medium was replaced by L-F12 containing 1 μM simvastatin (final concentration: 0.2% DMSO) or L-F12 free from simvastatin, and K1 was incubatted for 24 hours while M19 was incubated for 12 hours. On day 3, 50 μl of 1 mM [2-$^{14}$C] sodium acetate (20 μCi/flask) was added and after incubation for 6 hours, cells were washed with phosphate buffered saline (PBS) and solubilized in 2 ml of 0.1N NaOH. 50 μl of the cell solution was used for protein assay and the remainder was used for $^{14}$C-cholesterol assay. For $^{14}$C-cholesterol assay, the cell solution was first combined with 2 ml of ethanol solution containing 0.36 N NaOH and heat-treated at 80° C. for one hour. After cooling, the mixed solution was extracted with petroleum ether and concentrated under N$_2$ stream, thereafter cholesterol was separated by thin layer chromatography to measure the radioactivity of $^{14}$C-cholesterol on the plate as photostimulated luminescence (PSL) using BAS2000 (Fuji Film). Cellular protein level was measured by the BCA method and the cholesterol synthesis activity was expressed as the synthesized cholesterol amount in PSL per mg of the protein per 6 hours.

Figure 5:
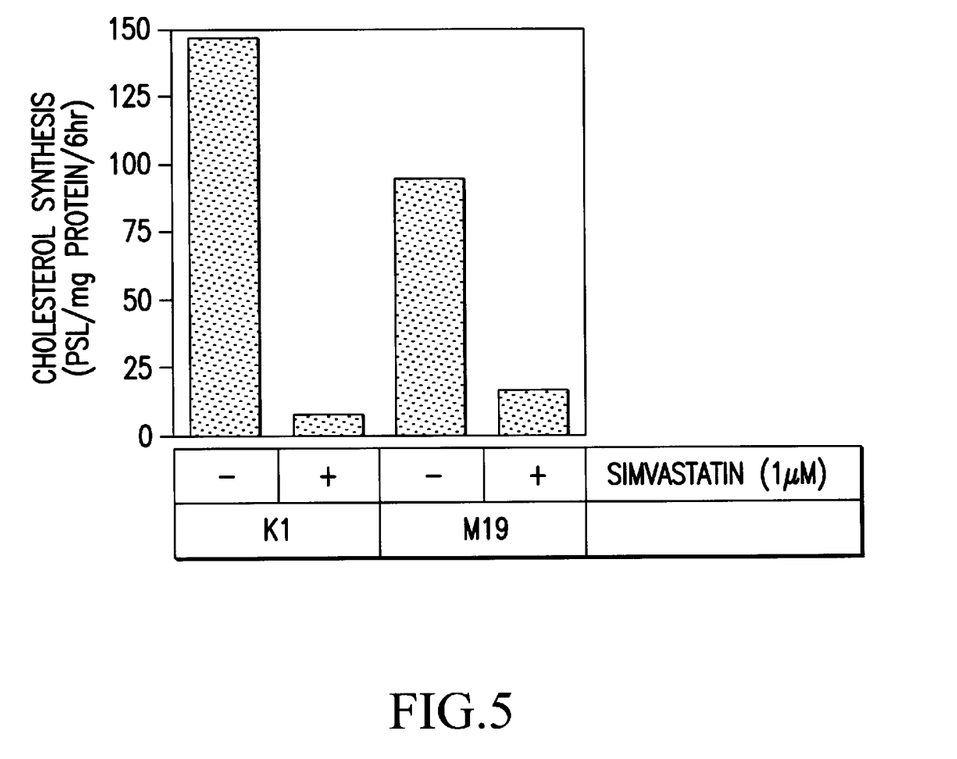
FIG. 5. A graph showing cholesterol synthesis activity in CHO-K1 cells and M19 cells in the presence or absence of simvastatin. Cholesterol synthesis activity was measured by the $^{14}C$-acetate incorporation assay.

As the results in FIG. 5, simvastatin inhibited cholesterol synthesis activity in both cell lines. Since S2P inhibitors are ineffective in S2P-deficient cells, a cholesterol synthesis activity assay using the two types of cell lines proved to be a useful system that can specifically detect S2P inhibitors, Example 4

Screening Method According to the Fourth Embodiment

PCR-amplified human SREBP-2 fragment (475-1141) having an XhoI site at its both ends was inserted into the XhoI site of a green fluorescence protein expression vector, pEGFP-C1 (Clontech). A sequence having a modified BspEI site at each end of T-large antigen-derived NLS (5'-cctaagaagaagaggaaggtt-3') was inserted into the BspEI site of the resulting pEGFP-SREBP2 (475-1141) to prepare pGNR. This was transferred into CHO-K1 or M19 by the FuGENE6 method (Boeringer Mannheim). 9 hours after transfection, the medium was replaced by L-F12 (in the presence or absence of 1 μg/ml 25-hydroxycholesterol and 10 μg/ml cholesterol), and after incubation overnight, fluorescence intensity of the nucleus was observed by a confocal laser scanning microscope.

As the results in Table 3, fluorescence was detected in the absence of sterol in the nucleus derived from CHO-K1 cells but not in M19. This demonstrated that SREBP pathway inhibitors could be specifically detected by treating cells carrying pGNR with a test drug and then observing fluorescence intensity of the nucleus.

TABLE 3

| Comparison of fluorescence intensities of the nuclei of cells carrying pGNR | | |
|---|---|---|
| | K1 | M19 |
| In the presence of sterol | − | − |
| In the absence of sterol | + | − |

Example 5

Screening Method According to the Fifth Embodiment

In the same manner as in Example 4, pGNR was transferred into CHO-K1 and 25RA, grown and observed.

As the results in Table 4, attenuated fluorescence was detected in the nucleus of CHO-K1 in the presence of sterol, but not in 25RA. This demonstrated that sterol-like SREBP pathway inhibitors can be specifically detected by observing 25RA and CHO-K1-derived cells in which pGNR has been introduced.

TABLE 4

Comparison of fluorescence intensities in the nuclei of cells carrying pGNR

|  | K1 | 25RA |
|---|---|---|
| In the presence of sterol | − | + |
| In the absence of sterol | + | ++ |

Example 6

Screening Method According to the Sixth Embodiment

Into pGNR digested with Bgl2 and Hind3 was inserted human SREBP-2 having a Bgl2 site and a Hind3 site with a stop codon at the PCR-amplified 5' end and 3' end (475–522), respectively, to prepare pGNT. This was transferred into 25RA and DM7 and incubated overnight in F-F12, and then fluorescence intensity of the nucleus was observed by a confocal laser scanning microscope in the manner as described in Example 4.

As the results in Table 5, intense fluorescence was detected in the nucleus of 25RA while the fluorescence in the nucleus of DM7 was weak. This demonstrated that S2P inhibitors can be specifically detected by observing fluorescence of the nucleus carrying pGNT and treated with a test drug.

TABLE 5

Comparison of fluorescence intensities of the nuclei of cells carrying pGNT

| 25RA | DM7 |
|---|---|
| +++ | +/− |

What is claimed is:

1. A screening method for inhibitors specific for sterol regulatory element binding protein (SREBP) pathway, which comprises the steps of:
   a) culturing each of
      (i) mutant cells in which SCAP has lost ability to respond to sterol levels, and
      (ii) normal cells in which SCAP has not lost ability to respond to sterol levels
      in the presence and absence of a test inhibitor of SREBP pathway, and
   b) measuring both cholesterol synthesis and LDL receptor synthesis of the cells,
   wherein,
      in cells (i), if cholesterol synthesis or LDL receptor synthesis is not decreased in cells cultured in the presence of the test inhibitor compared with cells cultured in the absence of the test inhibitor,
      while in cells (ii), if both cholesterol synthesis and LDL receptor synthesis are decreased in cells cultured in the presence of the test inhibitor compared with cells cultured in the absence of the test inhibitor,
      then the test inhibitor inhibits the SREBP pathway.

2. A screening method for inhibitors specific for sterol regulatory element binding protein (SREBP) pathway cleavage activating protein (SCAP), which comprises the steps of:
   a) culturing each of:
      (i) mutant cells in which SCAP has lost ability to respond to sterol levels, and
      (ii) normal cells in which SCAP has not lost ability to respond to sterol levels,
      in the presence and absence of a test inhibitor of SREBP pathway, and
   b) measuring either cholesterol synthesis or LDL receptor synthesis of both of cells (i) and (ii),
   wherein,
      in cells (i), if cholesterol synthesis or LDL receptor synthesis is not decreased in cells cultured in the presence of the test inhibitor compared with cells cultured in the absence of the test inhibitor,
      while in cells (ii), cholesterol synthesis or LDL receptor synthesis is decreased in cells cultured in the presence of the test inhibitor compared with cells cultured in the absence of the test inhibitor,
      then the test inhibitor inhibits SCAP.

3. A screening method for inhibitors specific for Site-2 protease (S2P) in the sterol regulatory element binding protein (SREBP) pathway, which comprises the steps of:
   a) culturing each of
      (i) S2P-deficient cells and
      (ii) S2P-carrying cells,
      in the presence and absence of a test inhibitor of SREBP pathway, and
   b) measuring either cholesterol synthesis or LDL receptor synthesis of both of the cells,
   wherein,
      if cholesterol synthesis or LDL receptor synthesis is lowered in S2P-carrying cells cultured in the presence of the test inhibitor compared with S2P-carrying cells cultured in the absence of the test inhibitor,
      while cholesterol synthesis or LDL receptor synthesis is no more lowered in S2P-deficient cells cultured in the presence of the test inhibitor compared with S2P-deficient cells cultured in the absence of the test inhibitor,
      then the test inhibitor inhibits Site-2 protease (S2P) in the SREBP pathway.

4. The method of claim 1, wherein said cells are those which have a mutation on an SREBP cleavage-activating protein (SCAP) whereby SREBP is cleaved by at site 1 even in the presence of excessive levels of sterols.

5. The method of claim 2, wherein said cells in which the cleavage of SREBP by S1P is not affected by sterols are those which have a mutation on an SREBP cleavage-activating protein (SCAP) whereby SREBP is cleaved by at site 1 even in the presence of excessive levels of sterols.

6. The method of claim 3, wherein both of said S2P-deficient and S2P carrying cells are those in which cleavage of SREBP by S1P is not affected by sterol levels.

7. The method of claim 3, wherein both of said S2P-deficient and S2P carrying cells are those in which cleavage of SREBP by S1P is affected by sterol levels.

* * * * *